US00PP15578P2

(12) United States Plant Patent
Zaiger et al.

(10) Patent No.: US PP15,578 P2
(45) Date of Patent: Feb. 22, 2005

(54) PEACH TREE PLANT NAMED 'SUPER LADY'

(50) Latin Name: *Prunus persica*
Varietal Denomination: Super Lady

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 92 days.

(21) Appl. No.: 10/810,182

(22) Filed: Mar. 29, 2004

(51) Int. Cl.[7] ..... A01H 5/00
(52) U.S. Cl. ..... Plt./197
(58) Field of Search ..... Plt./197

*Primary Examiner*—Anne Marie Grunberg

(57) ABSTRACT

A new and distinct variety of peach tree (*Prunus persica*). The following features of the tree and its fruit are characterized with the tree budded on 'Nemagaurd' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Fruit ripening in the early maturity season.
2. Fruit with good flavor and eating quality.
3. Having a low winter chilling requirement of approximately 350 hours at or below 45° F.
4. Fruit with firm, yellow flesh, good handling and shipping quality.
5. Heavy and regular bearing of fruit.

1 Drawing Sheet

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of peach tree was originated and asexually reproduced by us in our experimental orchard located near Modesto, Stanislaus County, Calif.

PRIOR VARIETIES

Among the existing varieties of nectarine and peaches, which are known to us, and mentioned herein, 'Earlirich' Peach (U.S. Plant Pat. No. 9,002), 'Super Rich' Peach (U.S. Plant Pat. No. 9,860), 'Ruby Gold' Nectarine (U.S. Plant Pat. No. 3,101), 'Fayette' Peach (non-patented) and 'Desert Gold' Peach (non-patented).

STATEMENT REGARDING FEDERALLY SPONSORED RESEARCH AND DEVELOPMENT:

Not applicable.

ORGIN OF THE VARIETY

The new variety of peach tree (*Prunus persica*) was originated by us in our experimental orchard located near Modesto, Calif. from a first generation cross between two proprietary seedlings with field identification numbers 171LE615 and 54Z432. The maternal parent (171LE615) was originated by us from a cross between the following varieties; 'Earlirich' Peach (U.S. Plant Pat. No. 9,002) and 'Super Rich' Peach (U.S. Plant Pat. No. 9,860). The paternal parent (54Z432) originated from crosses between the following varieties; 'Fayette' Peach (non-patented), 'Ruby Gold' Nectarine (U.S. Plant Pat. No. 3,101) and the proprietary numbered selection (64EF214). A large number of seedlings from this first generation cross were budded to older trees of 'Nemagaurd' Rootstock (non-patented), to accelerate rapid fruit production for evaluation. Under careful and close observation, one such budded seedling exhibited desirable fruit characteristics in the early maturity season and was selected in 2001 for additional asexual propagation and commercialization.

ASEXUAL REPRODUCTION OF THE VARIETY

Asexual reproduction of the new and distinct variety of peach tree was by budding to 'Nemagaurd' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new variety of peach is of large size, vigorous, upright growth and a productive and regular bearer of medium to large size, firm, yellow flesh, clingstone fruit with good flavor and eating quality. The fruit is further characterized by ripening in the early maturity season, having an attrative orange-red blush covering a rich, yellow skin color, and being relatively uniform in size throughout the tree. The tree is characterized by having a relatively low winter chilling requirement of approximately 350 hours at or below 45° F. In comparison to the low chilling variety 'Desert Gold' Peach (non-patented), the fruit is larger in size, has firmer flesh and is approximately 3 weeks earlier in maturity. In comparison to 'Super Rich' Peach (U.S. Plant Pat. No. 9,860) the fruit of the new variety is 1 week earlier in maturity and the tree requires approximately 350 hours less winter chilling at or below 45° F.

PHOTOGRAPH OF THE VARIETY

The accompanying color photographic illustration shows typical specimens of the foliage and fruit of the present new peach variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of peach tree, its flowers, foliage and fruit, as based on observations of 5 year old specimens grown near Modesto, Calif., with color in accordance with Munsell Book of Color.

Tree:

*Size.*—Large, normal for most low chill peach varieties. Pruned in height at maturity to 3 to 3½ meters for economical harvesting of fruit.

*Vigor.*—Vigorous, tree growth of 1.5 to 2 meters the first growing season. Varies with fertility, type of soil and cultural practices.

*Form.*—Upright, usually pruned to vase shape to allow more sunlight and air movement to center of tree.

*Branching habit.*—Upright, crotch angle approximately 30°, increases with heavy crop load.

*Productivity.*—Productive, normal fruit thinning and spacing necessary for desired marketable fruit. Fruit set varies with climatic conditions during bloom period.

*Bearer.*—Regular, adequate fruit set 3 consecutive years. No alternate bearing observed.

*Fertility.*—Self-fertile.

*Density.*—Medium dense, pruned to vase shape by opening center of tree which enhances fruit color and keeps fruit wood healthy.

*Hardiness.*—Hardy in all stone fruit growing areas of California. Winter chilling approximately 350 hours at or below 45° F.

Trunk:

*Size.*—Medium. Average circumference 47.5 cm at 20.0 cm above ground on a 5 year old tree.

*Stocky.*—Medium.

*Texture.*—Medium shaggy, becomes rougher with age.

*Color.*—Varies from 2.5Y 7/2 to 2.5Y 5/2.

Branches:

*Size.*—Medium. Average circumference 13.0 cm at 1.5 m above ground.

*Surface texture.*—New growth relatively smooth, becoming rougher with age. Old growth medium rough.

*Lenticels.*—Average number 44 in a 25.8 square cm area. Average length 5.1 mm. Average width 1.4 mm. Color varies from 2.5YR 6/8 to 5YR 5/8.

*Color.*—New growth varies from 2.5GY 6/6 to 2.5GY 5/8. Old growth varies from 5YR 4/6 to 5YR 3/6.

Leaves:

*Size.*—Large. Average length 147.5 mm. Average width 30.9 mm.

*Form.*—Lanceolate.

*Apex.*—Acuminate.

*Base.*—Cuneate.

*Margin.*—Crenate.

*Thickness.*—Medium.

*Surface texture.*—Upper surface relatively smooth, slightly indented over midrib and leaf veins. Lower surface relatively smooth, small ridges created by midrib and pinnate venation. Both surfaces glabrous.

*Petiole.*—Medium. Average length 9.2 mm. Average width 1.4 mm. Color varies from 5GY 7/6 to 5GY 6/6. Longitudinally grooved, surface glabrous.

*Glands.*—Globose. Small. Average length 0.6 mm. Average diameter 0.4 mm. Average number 2, varies from 1 to 2. Located primarily on base of leaf blade, some on upper portion of petiole. Color 2.5GY 5/6.

*Color.*—Upper surface varies from 5GY 4/6 to 5GY 3/6. Lower surface varies from 5GY 5/4 to 5GY 5/6. Midvein color 5GY 7/6.

Flower buds:

*Size.*—Large. Average length 19.3 mm. Average width 10.8 mm.

*Hardiness.*—Hardy in all stone fruit growing areas of California.

*Form.*—Conical, becoming elongated before opening.

*Pedicel.*—Medium. Average length 5.3 mm. Average width 1.1 mm. Color 2.5GY 7/8.

*Color.*—Varies from 5RP 7/10 to 5RP 7/8, varies with age of bud.

Flowers:

*Size.*—Large, showy. Average height 18.3 mm. Average diameter 32.2 mm.

*Petals.*—Number 5, alternatively arranged to sepals. Large. Average length 20.1 mm. Average width 19.6 mm. Shape — orbicular. Margin — sinuate, slightly cupped. Color varies from 5RP 8/6 to 5RP 7/8.

*Sepals.*—Number 5, alternately arranged to petals. Shape — ovate, apex rounded. Average length 6.5 mm. Average width 4.5 mm. Color — upper surface varies from 2.5GY 6/6 to 5RP 6/8. Lower surface varies from 7.5RP 3/6 to 7.5RP 3/8. Upper surface glabrous, lower surface pubescent.

*Stamens.*—Average number per flower 41. Average filament length 14.4 mm. Filament color varies from N 9.5/ to 2.5RP 9/2 as flowers age. Anther color varies from 10R 5/8 to 10R 5/10.

*Pollen.*—Self-fertile. Color — 2.5Y 7/12.

*Pistil.*—Usually 1, varies from 1 to 2. Surface — pubescent. Average length 17.8 mm. Average height compared to stamens, 0.7 mm higher. Color 2.5GY 9/4.

*Fragrance.*—Very slight.

*Blooming period.*—Date of first bloom Feb. 19, 2003. Date of petal fall Feb. 27, 2003. Varies slightly with climatic conditions.

*Color.*—5RP 8/6, fades as flowers mature.

*Number flowers per flower bud.*—One.

*Pedicel.*—Medium size. Average length 5.3 mm. Average width 1.3 mm. Color 2.5 GY 7/6.

Fruit:

*Maturity when described.*—Firm ripe.

*Date of first picking.*—May 5, 2003.

*Date of last picking.*—May 9, 2003. Varies slightly with climatic conditions.

*Size.*—Medium to large. Average diameter axially 57.1 mm. Average transversely in suture plane 63.0 mm.

Average weight 125.0 grams, average weight varies slightly with fertility of the soil, amount of thinning and climatic conditions.

*Form.*—Globose.

*Suture.*—Very shallow, extends from base to apex.

*Ventral surface.*—Nearly smooth, very slightly lipped.

*Apex.*—Nearly rounded, varies from rounded to slightly retuse.

*Base.*—Retuse.

*Cavity.*—Rounded to slightly elongated in suture plane. Average depth 3.5 mm. Average breadth 12.8 mm.

Stem:

*Size.*—Medium. Average length 7.9 mm. Average diameter 3.2 mm.

*Color.*—Varies from 2.5GY 6/8 to 5GY 6/6.

Flesh:

*Ripens.*—Evenly.

*Texture.*—Firm.

*Fibers.*—Few, small, tender.

*Firmness.*—Firm, has greater firmness than 'Desert Gold' Peach (non-patented).

*Aroma.*—Moderate.

*Amydgalin.*—Undetected.

*Eating quality.*—Good.

*Flavor.*—Good, with a good balance between acid and sugar.

*Juice.*—Moderate.

*Brix.*—Average 9.5°, varies slightly with amount of fruit per tree and climatic conditions.

*Color.*—Varies from 2.5Y 8.5/10 to 5Y 8/8. Pit cavity varies from 2.5Y 8/10 to 2.5Y 7/12.

Skin:

*Thickness.*—Medium.

*Surface.*—Smooth.

*Pubescence.*—Moderate amount, short.

*Tendency to crack.*—None.

*Color.*—Ground color varies from 10YR 7/10 to 2.5Y 8/8. Approximately 55% overspread with 5R 4/8 to 7.5R 4/8.

*Tenacity.*—Tenacious to the flesh.

*Astringency.*—None.

Stone:

*Type.*—Clingstone.

*Size.*—Medium to large. Average length 31.7 mm. Average width 20.5 mm. Average thickness 17.4 mm.

*Form.*—Ovoid.

*Base.*—Flat.

*Apex.*—Pointed. Average length 1.5 mm.

*Surface.*—Pitted throughout, pit cavities vary from round to slightly elongated. Furrows creating ridges toward apex on upper portion of stone.

*Sides.*—Unequal, one side slightly larger, extending further from suture plane.

*Ridges.*—Relatively smooth.

*Tendency to split.*—Very slight.

*Color.*—Varies from 10YR 7/4 to 10YR 6/6 when dry.

Kernal:

*Form.*—Ovoid.

*Taste.*—Bitter.

*Viability.*—Non-viable, incomplete embryo.

*Size.*—Medium. Average length 12.2 mm. Average width 10.5 mm. Average thickness 5.0 mm.

*Skin color.*—5Y 9/2 when dry.

Use: Dessert. Market—local and long distance.

Keeping quality: Good, held firm in cold storage 2 weeks at 38° to 42° F. without internal breakdown or appreciable loss of flavor.

Shipping quality: Good, minimal skin scarring or bruising of flesh during picking and packing trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

It is claimed:

1. A new and distinct variety of peach tree, substantially as illustrated and described, characterized by its large size, vigorous, upright growth, and being a regular and productive bearer of medium to large size, early maturing, yellow flesh, clingstone fruit with good flavor and eating quality. The fruit is further characterized by having firm flesh, an attractive orange-red blush covering the rich, yellow skin color with good handling and shipping qualities and in comparison to the variety 'Super Rich' Peach (U.S. Plant Pat. No. 9,860), the tree of the new variety requires approximately 350 hours less winter chilling and its fruit matures approximately 7 days earlier.

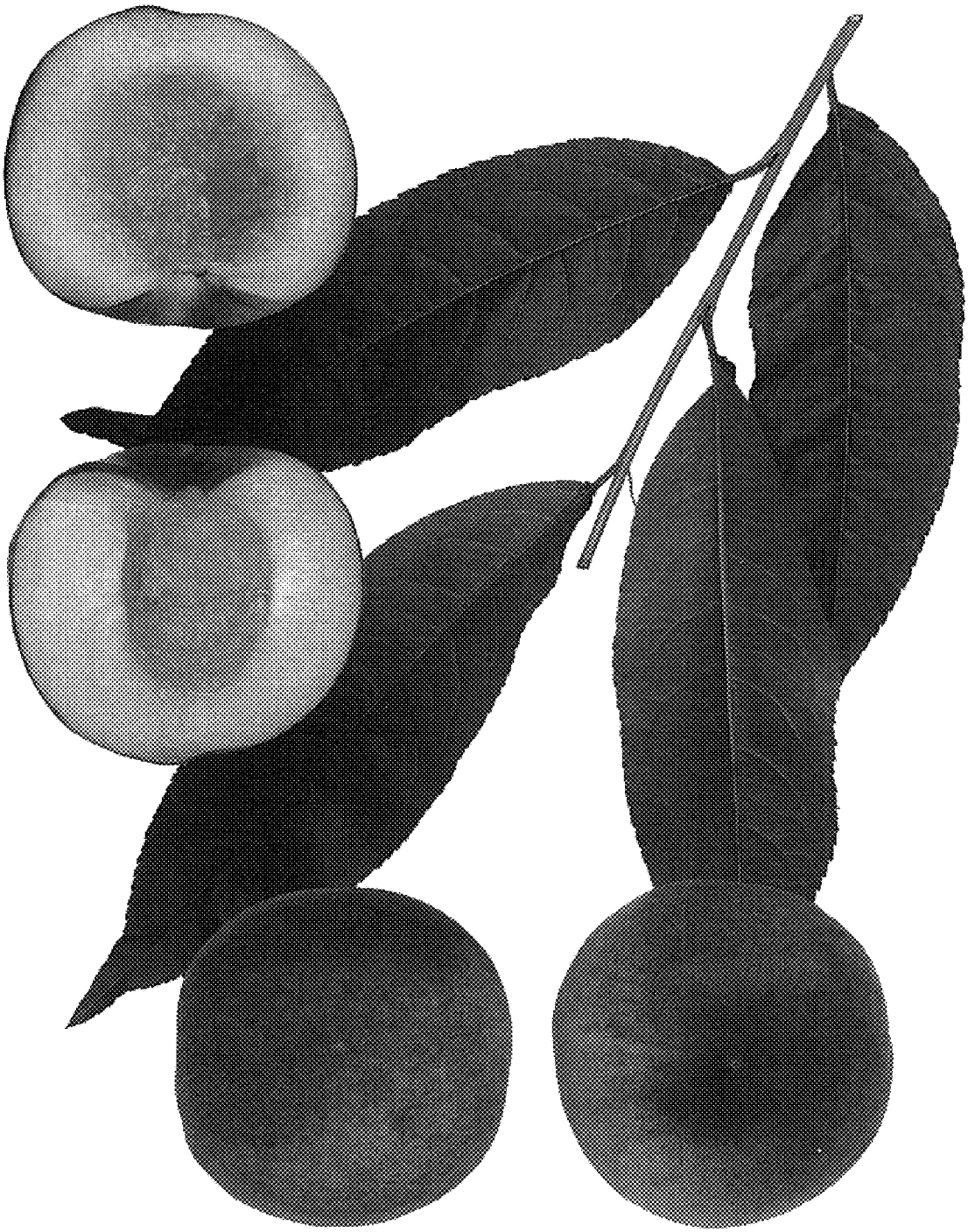

* * * * *